United States Patent [19]

Nabata

[11] Patent Number: 4,812,566
[45] Date of Patent: Mar. 14, 1989

[54] PROCESS FOR PREPARING 1-DODECYLAZACYCLOHEPTANE-2-ONE

[75] Inventor: Toshinari Nabata, Kobe, Japan

[73] Assignee: KOEI Chemical Co., Ltd., Osaka, Japan

[21] Appl. No.: 134,381

[22] Filed: Dec. 17, 1987

[30] Foreign Application Priority Data

Dec. 24, 1986 [JP] Japan ................... 61-314501

[51] Int. Cl.⁴ ......................... C07D 223/10
[52] U.S. Cl. ........................ 540/533; 540/451
[58] Field of Search ................. 540/533, 451

[56] References Cited

U.S. PATENT DOCUMENTS 4,422,970 12/1983 Rajadhyaksha et al. ........... 540/533

FOREIGN PATENT DOCUMENTS 0095096 11/1983 European Pat. Off. ............ 540/533

Primary Examiner—Robert T. Bond

Attorney, Agent, or Firm—Armstrong, Nikaido, Marmelstein & Kubovcik

[57] ABSTRACT

Disclosed is a process for preparing 1-dodecylazacycloheptane-2-one, the process comprising reacting azacycloheptane-2-one with dodecyl halide in a substantially non-aqueous system in the presence of a phase-transfer catalyst represented by the formula

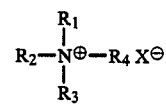

wherein $R_1$, $R_2$, $R_3$ and $R_4$ are alkyl or aralkyl, or two or three of the groups $R_1$, $R_2$, $R_3$ and $R_4$, when taken together with nitrogen to which they are attached, form a heterocyclic group (in which case the remaining one or two of the groups being alkyl or aralkyl) and $X^\ominus$ is a univalent anion.

12 Claims, No Drawings

PROCESS FOR PREPARING 1-DODECYLAZACYCLOHEPTANE-2-ONE

The present invention relates to a process for preparing 1-dodecylazacycloheptane-2-one, and more particularly to a process for preparing 1-dodecylazacycloheptane-2-one by reacting azacycloheptane-2-one with dodecyl halide.

1-Dodecylazacycloheptane-2-one is a compound useful as an agent for the promotion of percutaneous absorption which assists the absorption of a drug such as an anti-inflammatory through the skin.

Among known processes for preparing 1-dodecylazacycloheptane-2-one is a process comprising the steps of reacting azacycloheptane-2-one with an alkali metal hydride to synthesize an alkali salt of azacycloheptane-2-one and reacting the alkali salt thereof with dodecyl bromide (Japanese Unexamined Patent Publication No. 1,035/1977). This process gives 1-dodecylazacycloheptane-2-one in a yield of 80%, but the process is economically disadvantageous because it needs to use an alkali metal hydride which is expensive and it requires a reaction time of as long as 20 hours.

Also known as such process is a process involving the reaction of azacycloheptane-2-one with excess dodecyl bromide in a mixed solvent of an aromatic hydrocarbon and water in the presence of a phase-transfer catalyst (Japanese Unexamined Patent Publication No. 210,066/1983). This process, however, requires large amounts of water and sodium hydroxide, more specifically water in an amount corresponding to about 15 times the weight of azacycloheptane-2-one, and 22 moles of sodium hydroxide serving as a receptor for hydrogen halide per mole of the dodecyl halide. Consequently the process has the disadvantage of being significantly low in the productive efficiency with respect to the volume of the reaction vessel. Further, the process proceeds at a low reaction rate and requires a reaction time of at least 100 hours to prepare 1-dodecylazacycloheptane-2-one in a yield of 90% or more, hence extremely inefficient. Experimentally we practiced the process disclosed in Japanese Unexamined Patent Publication No. 210,066/1983 and found that the process produces a large amount of dodecyl ether as a by-product (see Comparison Example 1 to be described later) which is similar in boiling point to 1-dodecylazacycloheptane-2-one. Accordingly said conventional process is disadvantageous in that it is difficult to obtain high-purity 1-dodecylazacycloheptane2-one by effecting a simple distillation operation for purification.

It is an object of the present invention to provide a process for preparing high-purity 1-dodecylazacycloheptane-2-one in a high yield, the process being capable of completing the reaction within a short period of time using relatively inexpensive starting materials.

It is another object of the invention to provide a process for preparing 1-dodecylazacycloheptane-2-one in which a by-product that is difficult to separate is produced in such a small amount that the obtained 1-dodecylazacycloheptane-2-one is easily purified.

Other features and objects of the present invention will become apparent from the following description.

The present invention provides a process for preparing 1-dodecylazacycloheptane-2-one, the process comprising reacting azacycloheptane-2-one with dodecyl halide in a substantially non-aqueous system in the presence of a phase-transfer catalyst represented by the formula

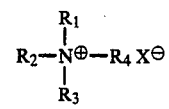

wherein $R_1$, $R_2$, $R_3$ and $R_4$ are alkyl or aralkyl, or two or three of the groups $R_1$, $R_2$, $R_3$ and $R_4$, when taken together with nitrogen to which they are attached, form a heterocyclic group (in which case the remaining one or two of the groups is alkyl or aralkyl) and $X^\ominus$ is a univalent anion.

The process of the present invention comprises reacting azacycloheptane-2-one with dodecyl halide in a substantially non-aqueous system, and can produce 1-dodecylazacycloheptane-2-one in higher yields within a shorter period of time than the conventional process for preparing the same in which these two compounds are reacted in a water-containing solvent. Moreover, since the process of the present invention gives a markedly small amount of by-product, the contemplated compound can be easily separated from the reaction product, that is to say, high-purity 1-dodecylazacycloheptane-2-one can be obtained by simple distillation means for purification. The process of the invention need not use large amounts of a solvent and other additives and it is possible to react the starting materials, i.e. azacycloheptane-2-one and dodecyl halide in substantially equimolar amounts. Thus the process of the invention is remarkably advantageous in terms of production costs.

The phase-transfer catalyst useful in the process of the present invention is one represented by the formula

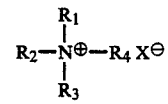

wherein $R_1$, $R_2$, $R_3$ and $R_4$ and $X^\ominus$ are as defined above.

Of the alkyl groups represented by $R_1$, $R_2$, $R_3$ and $R_4$, preferable are those having 1 to 12 carbon atoms such as methyl, ethyl, propyl, butyl, octyl, lauryl and the like.

Preferred examples of aralkyl groups are benzyl, phenethyl and like phenyl $C_1$–$C_3$ alkyl groups.

Two or three of the groups $R_1$, $R_2$, $R_3$ and $R_4$, together with nitrogen to which they are attached, may form a heterocyclic group. Examples of preferred heterocyclic groups are 5 or 6-membered, saturated or unsaturated heterocyclic groups containing one nitrogen atom such as pyrrolidyl, piperidino, pyridyl, picolyl and the like.

The univalent anion represented by $X^\ominus$ can be any of univalent anions commonly used for phase-transfer catalysts. Preferred examples of univalent anions are halogen anions such as $Cl^\ominus$, $Br^\ominus$ and $I^\ominus$, $OSO_3H^\ominus$, hydroxyl anion, perchlorate anion and the like. Among these anions, $Cl^\ominus$, $Br^\ominus$, $OSO_3H^\ominus$ and the like are more preferred.

Suitable examples of the phase-transfer catalyst of said formula are quaternary ammonium salts widely used in industries such as tetramethylammonium chloride, benzyltrimethylammonium chloride, benzyltriethylammonium chloride, tetrabutylammonium bromide, tetrabutylammonium hydrogensulfate, trioctylmethylammonium chloride, N-laurylpyridinium chloride, N-laurylpicolinium chloride and the like. Among these examples, tetrabutylammonium bromide and tetrabutylammonium hydrogensulfate are preferred.

The amount of the catalyst used is in the range of about 1 to about 20 mole %, preferably about 1 to about 5 mole % based on the azacycloheptane-2-one. The reaction rate can be increased by using a large amount of the catalyst within said range.

It is preferred to use a catalyst in a non-aqueous form because the reaction is carried out in a substantially non-aqueous system. The non-aqueous form of the catalyst tb be used in the invention varies with the type of the catalyst and includes crystalline, wax and like forms. If the amount of the catalyst used is as small as about 1 to about 5 mole % based on the azacycloheptane-2-one, the catalyst containing about 20 to about 70% by weight of water is used so that up to about 2% by weight of water may be present in the reaction system. The presence of such amount of water does not seriously affect the reaction and brings about only a small degree of reduction in yields. Thus the use of such water-containing catalyst is allowable according to the present invention.

Examples of dodecyl halides useful in the present invention are dodecyl chloride, dodecyl bromide, dodecyl iodide, etc. The amount of the dodecyl halide used is in the range of about 0.8 to about 2.0 moles per mole of the azacycloheptane-2-one. Even if the dodecyl halide is used in an amount of about 0.9 to about 1.1 moles per mole thereof, i.e. in substantially equimolar amount, the reaction can smoothly proceed.

The process of the present invention is carried out in a substantially non-aqueous sytem. The type of the solvent is not specifically limited insofar as the solvent is an inactive organic one. Examples of such solvent are benzene, toluene, xylene, cyclohexane, hexnne, octane and like hydrocarbons, dioxane, tetrahydrofuran and like ethers.

Of the organic solvents exemplified above, preferred are benzene, toluene, xylene and like aromatic hydrocarbons among which toluene is more preferred. The amount of the solvent used is equal to or in excess of the total weight of the two starting materials, namely azacycloheptane-2-one and dodecyl halide. A suitable amount of the solvent is 1 to 3 times the total weight of the starting materials in view of the productive efficiency with respect to the volume of the reaction vessel.

It is most preferred to conduct the reaction in the process of the present invention without any amount of water. However, the reaction of the invention can be carried out in the presence of water in an amount as small as that contained in the catalyst, and the reaction system may contain up to about 2% by weight of water.

A base is preferably used as a receptor for hydrogen halide in order to make the progress of the reaction smoother. Examples of useful bases are hydroxides of alkali metals such as sodium hydroxide, potassium hydroxide and the like or hydroxides of alkaline earth metals such as calcium hydroxide, magnesium hydroxide and the like. The base useful in the invention is in the form of flakes, powders or the like and, in use, is added directly to the reaction system. A more preferable base is flaky sodium hydroxide. According to the present invention, the contemplated compound can be produced in high yields within a short period of time by using the base in an amount of at least about 2 moles per mole of the dodecyl halide. The amount of the base used is preferably about 2 to about 10 moles, more preferably about 2 to about 5 moles, per mole of the dodecyl halide.

The reaction of the present invention is carried out at a temperature of about 20° to about 120° C., preferably about 50° to about 90° C.

The reaction time is variable depending on the reaction temperature and on the amount of the catalyst. Yet about 1 to about 10 hours of reaction is sufficient in the practice of the present invention.

Since the process of the present invention gives a markedly small amount of dodecyl ether as a by-product, high-purity 1-dodecylazacycloheptane-2-one can be obtained with extreme ease by conventional separation methods, e.g. by adding water to the reaction mixture to dissolve the inorganic materials in water, and distillating the separated oil layer for purification.

According to the present invention, the reaction is conducted in a substantially non-aqueous system and 1-dodecylazacycloheptane-2-one can be produced more efficiently within a shorter period of time than conventional processes. For example, a conventional process requires 30 hours of reaction until completion to produce the desired compound in a yield of 82.3% based on the azacycloheptane-2-one (see Comparison Example 1). On the other hand, the reaction of the present invention is completed in about 10 hours, giving the desired compound in a yield of 99.6% (see Example 1) which is higher than the yield resulting from said conventional process.

Since the process of the present invention affords a markedly small amount of dodecyl ether as a by-product, purification is easy and high-purity 1-dodecylazacycloheptane-2-one can be obtained, for example, by simple distillation operation for purification.

According to the invention, a reaction using the starting materials in a mole ratio of about 1.0 which is desirable in terms of production costs can be advantageously performed (see Examples 3 to 5).

The present invention will be described below in greater detail with reference to the following Examples and Comparison Examples to which, however, the invention is limited in no way.

EXAMPLE 1

A 1l reactor is charged with 34 g (0.3 mole) of azacycloheptane-2-one, 112 g (0.45 mole) of dodecyl bromide, 300 g of toluene, 3.4 g (3.3 mole % based on the azacycloheptane-2-one) of crystalline tetrabutylammonium hydrogensulfate (TBAHS) and 90 g (2.25 moles) of flaky sodium hydroxide. This heterogeneous mixture was stirred at 50° C. for 10 hours. After the mixture was cooled to 40° C., 135 g of water was added to the mixture, followed by stirring at 40° C. for 30 minutes.

The oil layer was separated and the oil layer thus obtained was subjected to distillation, giving 84.0 g of 1-dodecylazacycloheptane-2-one having a boiling point of 195° to 200° C./3 mmHg (yield of 99.6% based on the azacycloheptane-2-one), and also 0.8 g of dodecyl ether (yield of 1.0% based on the dodecyl bromide).

COMPARISON EXAMPLE 1

The same procedure as in Example 1 was repeated with the exception of using 360 g (4.50 moles) of a 50% aqueous solution of sodium hydroxide in place of the flaky sodium hydroxide used in Example 1. This heterogeneous mixture was stirred at 50° C. for 30 hours. The same aftertreatment as in Example 1 was performed, giving 69.4 g of 1-dodecylazacycloheptane-2-one (yield of 82.3% based on the azacycloheptane-2-one) and 10.0 g of dodecyl ether (yield of 12.6% based on the dodecyl bromide).

COMPARISON EXAMPLE 2

A 46.0 g quantity of 1-dodecylazacycloheptane-2-one (yield of 54.6% based on the azacycloheptane-2-one) and 5.0 g of dodecyl ether (yield of 6.3% based on the dodecyl bromide) were produced by conducting the same reaction and the same aftertreatment as in Comparison Example 1 with the exception of changing the reaction time of COMPARISON EXAMPLE 1 to 10 hours.

EXAMPLE 2

The same procedure as in Example 1 was repeated with the exception of using as the catalyst each of the following crystalline compounds; tetrabutylammonium bromide (TBAB), benzyltriethylammonium chloride (BTEAC) and tetramethylammonium chloride (TMAC). Table 1 below shows the results.

TABLE 1

| Catalyst | TBAHS (*2) | TBAB | BTEAC | TMAC |
|---|---|---|---|---|
| Amount of catalyst (*1) | 3.4 g (3.3%) | 3.4 g (3.5%) | 3.4 g (5.0%) | 3.4 g (10.4%) |
| Reaction time | 10 hrs | 10 hrs | 10 hrs | 10 hrs |
| Amount of compound obtained | 84.0 g | 84.1 g | 74.9 g | 58.3 g |
| Yield (based on the azacycloheptane-2-one) | 99.6% | 99.8% | 88.8% | 69.2% |

Note:
(*1) Mole % based on the azacycloheptane-2-one
(*2) Example 1

EXAMPLE 3

A 1l reactor was charged with 57 g (0.5 mole) of azacycloheptane-2-one, 125 g (0.5 mole) of dodecyl bromide, 182 g of toluene, 3.2 g (2 mole %) of crystalline tetrabutylammonium bromide (TBAB) and 60 g (1.5 moles) of flaky sodium hydroxide. This heterogeneous mixture was stirred at 50° C. for 10 hours. The same aftertreatment as in Example 1 was repeated, giving 133.5 g of 1-dodecylazacycloheptane-2-one (yield of 95.0%) and 0.7 g of dodecyl ether (yield of 0.8%)

EXAMPLE 4

The same reaction as in Example 3 was repeated with the exception of changing the reaction temperature of Example 3 to 70° C. and the reaction time thereof to 5 hours, followed by the same aftertreatment, giving 134.2 g of 1-dodecylazacycloheptane-2-one (yield of 95.5%) and 0.7 g of dodecyl ether (yield of 0.8%).

EXAMPLE 5

The same reaction as in Example 3 was repeated with the exception of changing the reaction temperature of Example 3 to 90° C. and the reaction time thereof to 3 hours, followed by the same aftertreatment, giving 133.0 g of 1-dodecyaazacycloheptane-2-one (yield of 94.7%) and 0.9 g of dodecyl ether (yield of 1.0%).

EXAMPLE 6

The same reaction as in Example 4 was repeated with the exception of using 6.4 g (2 mole %) of a 50% aqueous solution of tetrabutylammonium bromide (TBAB) as the catalyst in place of crystalline TBAB used in Example 4, followed by the same aftertreatment, giving 131.4 g of 1-dodecylazacycloheptane-2-one (yield of 93.5%) and 1.5 g of dodecyl ether (yield of 1.7%).

EXAMPLE 7

The same reaction as in Example 4 was repeated with the exception of using 102 g (0.5 mole) of dodecyl chloride in place of the dodecyl bromide and changing the reaction time of Example 4 to 10 hours, followed by the same aftertreatment, giving 133.8 g of 1-dodecylazacycloheptane-2-one (yield of 95.2%) and 0.4 g of dodecyl ether (yield of 0.5%).

I claim:

1. A process for preparing 1-dodecylazacycloheptane-2-one comprising reacting azacycloheptane2-one with dodecyl halide in a substantially non-aqueous system in the presence of a phase-transfer catalyst represented by the formula:

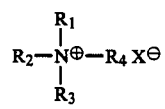

wherein $R_1$, $R_2$, $R_3$ and $R_4$ are selected from the group consisting of alkyl having 1 to 12 carbon atoms and phenyl-$C_1$-$C_3$-alkyl group, and two or three of the groups $R_1$, $R_2$, $R_3$ and $R_4$, when taken together with the nitrogen to which they are attached, form a 5- or 6-membered, saturated or unsaturated heterocyclic group containing one nitrogen atom, and $X^-$ is an anion selected from the group consisting of a halogen, hydrogensulfate, hydroxyl and perchlorate.

2. A process according to claim 1 wherein at least one aromatic hydrocarbon selected from the group consisting of benezene, toluene and xylene is used as a solvent.

3. A process according to claim 1 wherein toluene is used as a solvent.

4. A process according to claim 1 wherein the reaction is carried out in the presence of a base in an amount of about 2 moles or more per mole of the dodecyl halide.

5. A process according to claim 1 wherein the reaction is carried out in the presence of a base in an amount of about 2 to about 10 moles per mole of the dodecyl halide.

6. A process according to claim 5 wherein the base is flaky sodium hydroxide.

7. A process according to claim 1 wherein the phase-transfer catalyst is at least one species selected from the group consisting of tetramethylammonium chloride, benzyltrimethylammonium chloride, benzyltriethylammonium chloride, tetrabutylammonium bromide, tetrabutylammonium hydrogensulfate, trioctylmethylammonium chloride, N-laurylpyridinium chloride and N-laurylpicolinium chloride.

8. A process according to claim 7 wherein the phase-transfer catalyst is tetrabutylammonium bromide and/or tetrabutylammonium hydrogensulfate.

9. A process according to claim 1 wherein the dodecyl halide is used in an amount of about 0.8 to about 2.0 moles per mole of the azacycloheptane-2-one 10. A process according to claim 1 wherein the phase-transfer catalyst is used in an amount of about 1 to about 20 mole % based on the azacycloheptane-2-one.

11. A process according to claim 1 wherein the phase-transfer catalyst is used in an amount of about 1 to about 5 mole % based on the azacycloheptane-2-one.

12. A process according to claim 1 wherein the reaction of azacycloheptane-2-one with dodecyl halide is carried out in the reaction system containing up to 2% by weight of water.

* * * * *